United States Patent [19]

Azzazy et al.

[11] Patent Number: 5,349,187
[45] Date of Patent: Sep. 20, 1994

[54] METHOD AND APPARATUS FOR DETECTING VEHICLE OCCUPANTS UNDER THE INFLUENCE OF ALCOHOL

[75] Inventors: Medhat T. Azzazy, Laguna Niguel; Ali Dabiri, San Diego, both of Calif.

[73] Assignee: Science Applications International Corporation, San Diego, Calif.

[21] Appl. No.: 146,352

[22] Filed: Nov. 1, 1993

[51] Int. Cl.$^5$ .................. G01N 21/01; G01N 21/17
[52] U.S. Cl. .......................... 250/338.5; 250/340; 250/343
[58] Field of Search .............. 250/338.5, 340, 341, 250/343; 356/436, 437; 128/719; 340/576

[56] References Cited

U.S. PATENT DOCUMENTS

| | | | |
|---|---|---|---|
| 3,562,524 | 2/1971 | Moore et al. | 250/343 |
| 3,792,272 | 2/1974 | Harte et al. | 250/343 |
| 4,268,751 | 5/1981 | Fritzlen et al. | 250/343 |
| 4,410,273 | 10/1983 | Mantz et al. | 250/345 X |
| 4,613,845 | 9/1986 | DuBois | 340/576 |
| 4,716,413 | 12/1987 | Haile | 340/576 X |
| 4,749,553 | 6/1988 | Lopez et al. | 128/719 X |
| 4,905,498 | 3/1990 | O'Donnell et al. | 340/576 X |
| 4,924,095 | 5/1990 | Swanson, Jr. | 250/338.5 |
| 4,963,023 | 10/1990 | Goldovsky et al. | 250/338.5 X |
| 5,055,268 | 10/1991 | Martin | 128/719 X |
| 5,210,702 | 5/1993 | Bishop et al. | 250/338.5 X |
| 5,267,019 | 11/1993 | Whittaker et al. | 250/343 X |

OTHER PUBLICATIONS

Reid, et al., "High sensitivity point monitoring of atmospheric gases employing tunable diode laser", *Applied Optics*, vol. 17:11, pp. 1806–1810 (Jun. 1978).
Bjorklund, "Frequency-modulation spectroscopy: a new method for measuring weak absorptions and dispersions", *Optical Society of America*, vol. 5:1, pp. 15–17 (Jan. 1980).
Reid, et al., "Second-harmonic detectioin with tunable diode lasers-Comparison of experiment and lasers", *Appl. Phys.*, vol. B 26, pp. 203–210 (1981).
Schiff, et al., "Tunable diode laser systems for measuring trace gases in tropospheric air", *Environ. Sci. Technol.*, vol. 17:8, pp. 352A–364A (1983).
Tran, et al., "Frequency-modulation spectroscopy with a pulsed dye laser: experimental investigations of sensitivity and useful features", *Applied Optics*, vol. 23:9, pp. 1353–1360 (May 1984).
Lenth, "High frequency heterodyne spectroscopy with current-modulated diode lasers", *IEEE Journal of Quantum Electronics*, vol. QE-20:9, pp. 1046–1050 (Sep. 1984).
Gehrtz, et al., "High-frequency-modulation spectroscopy with a lead-salt diode laser", *Optics Letters*, vol. 11:3, pp. 132–134 (Mar. 1986).
Cooper, et al., "Two-tone optical heterodyne spectroscopy with a tunable lead-salt diode laser", *Optics Letters*, vol. 11:10, pp. 606–608 (Oct. 1986).
Fluckiger, et al., "Optical autodyne detection: theory and experiment", *Applied Optics*, vol. 26:2, pp. 318–325 (Jan. 1987).
Sachse, et al., "Fast-response, high-precision carbon monoxide sensor using a tunable diode laser absorption technique", *Journal of Geophysical Research*, vol. 92:D2, pp. 2071–2081 (Feb. 20, 1987).
Cooper, et al., "Two-tone optical heterodyne spectroscopy with diode lasers: theory of line shapes and experimental results", *J. Opt. Soc. Am.*, vol. 4:4, pp. 470–480 (Apr. 1987).
Chou, et al., "Single-tone and two-tone AM-FM spectral calculations for tunable diode laser adsorption spec- (List continued on next page.)

*Primary Examiner*—Constantine Hannaher
*Assistant Examiner*—Edward J. Glick
*Attorney, Agent, or Firm*—Fitch, Even, Tabin & Flannery

[57] ABSTRACT

A system for non-intrusive drunk driver screening comprising a wavelength modulated laser, harmonic detector, and signal analyzer apparatus for quantitative absorption spectroscopy detection of low level concentrations of alcohol molecules in a contained gaseous volume within the operator compartment of vehicles.

18 Claims, 2 Drawing Sheets

OTHER PUBLICATIONS troscopy", *Applied Optics*, vol. 27:17, pp. 3584–3587 (Sep. 1987).

Cooper, et al., "Frequency modulation spectroscopy with lead-salt diode lasers: a comparison of single-tone and two tone techniques", *Applied Optics*, vol. 26:17, pp. 3726–3732 (Sep. 1987).

Wang, et al., "Comparison of approaches to modulation spectroscopy with GaAlAs semiconductor laser: application to water vapor" *Applied Optics*, vol. 27:10 pp. 2071–2077 (May 1988).

Silver, et al., "Optical interference fringe reduction in laser absorption experiments", *Applied Optics*, vol. 27:10, pp. 1914–1916 (May 1988).

Silver, et al., "Two-tone optical heterodyne spectroscopy isng buried double heterostructure lead-sald diode lasers", *Applied Optics*, vol. 27:21, pp. 4438–444 (Nov. 1988).

Ouyang, et al., "Reliable and effiucient program for fitting Galatry and Voight profiles to spectral data on multiple lines", *Applied Optics*, vol. 28, pp. 1538–1545 (Apr. 1989).

Spartz, et al., "Evaluation of a mobile FT-IR system for rapid VOC determination", *American Environmental Laboratory*, pp. 15–30 (Nov. 1989).

Werle, et al., "Wideband noise characteristics of a lead-salt diode laser: possibility of quantum noise limited TDLAS performance", *Applied Optics*, vol. 28:9, pp. 1638–1642 (May 1989).

Carlisle, et al., "Quantum noise-limited FM spectroscopy with a lead-salt diode laser", *Applied Optics*, vol. 28:13, pp. 2567–2576 (Jul. 1989).

Chou, et al., "Optical fringe reduction technique for FM laser spectroscopy", *Applied Optics*, vol. 28:23, pp. 4973–4975 (Dec. 1989).

Hayward, et al., "High-sensitivity transient spectroscopy using tunable diode lasers", *Applied Physics B*, vol. 48:25–29 (1989).

Werle, et al., "Quantum-limited FM-spectroscopy with a lead-salt diode laser", *Appl. Phys. B*, vol. 49:99–108 (1989).

Bruce, et al., "Detection of oxygen using short external cavity GaAs semiconductor diode lasers", *Applied Optics*, vol. 29:9, pp .1327–1332 (Mar. 1990).

Lee, et al., "Tunable diode laser spectroscopy for isotope analysis-detection of isotopic carbon monoxide in exhaled breath", *IEEE Transactions on Biomedical Engineering*, vol. 38:10, pp. 966–973 (Oct. 1991).

Philippe, et al., "Tunable diode laser absorption sensor for temperature and velocity measurements of $O_2$ in air flows", *Department of Mechanical Engineering*, Stanford University (Calif.) pp.

Silver, "Frequency-modulation spectroscopy for trace species detection: theory and comparison among experimental methods", *Applied Optics*, vol. 31:6, pp. 707–717 (Feb. 1992).

Bomse, et al., "Frequency modulation and wavelength modulation spectroscopies: comparison of experimental methods using lead-salt diode laser", *Applied Optics*, vol. 31:6, pp. 718–731 (Feb. 1992).

METHOD AND APPARATUS FOR DETECTING VEHICLE OCCUPANTS UNDER THE INFLUENCE OF ALCOHOL

FIELD OF INVENTION

The present invention generally relates to the real-time detection of concentrations of airborne alcohol molecules and, more particularly, to a method and system for rapidly and reliably detecting the concentrations of airborne alcohol molecules in the interior compartments of vehicles to detect persons in such vehicles under the influence of alcohol.

BACKGROUND OF INVENTION

Enforcement of drunk driving statutes is of ever increasing importance. One current procedure used by law enforcement departments to enforce such statutes is to establish randomly located sobriety check points and to there evaluate vehicle operators for alcohol abuse. Unfortunately, the procedures currently used at such check points are generally inefficient and almost always impede the flow of traffic, thereby limiting the number of vehicles which can be surveyed.

Current sobriety evaluation methods which may be reliable and quantitative involve physically invasive processes of sampling and analyzing breath, blood or urine of the vehicle operator. Such processes are time consuming and often objectionable to the vehicle operator. Further, the validity of such testing is often questioned. As a result, sobriety check points often rely on qualitative non-invasive procedures such as visual observation and simple coordination tests to reduce the time for each evaluation. Such qualitative non-invasive procedures are subject to large errors. Published data have shown that only about half of the drivers operating motor vehicles while under the influence of alcohol are detected even by well trained observers.

Accordingly, an alternative means of sobriety checking is needed to eliminate traffic disruption and to substantially improve upon the low detection rate and low probability of detection of a driver operating a vehicle while under the influence of alcohol. The present invention satisfies such needs.

SUMMARY OF INVENTION

A person under the influence of alcohol exhales alcohol molecules ($CH_2CH_3OH$). When an intoxicated person is confined within the passenger compartment in a motor vehicle, the exhaled alcohol molecule concentration increases as a function of time. If the person in the vehicle passenger compartment is under the influence of alcohol near or in excess of the statutory limit, the concentration of exhaled alcohol molecules in the contained volume of air has been found to be as high as 3 parts per million (ppm) within 20 minutes. This level may drop to approximately 0.5 ppm if the windows are opened.

The present invention uses laser technology and absorption spectroscopy to non-invasively, rapidly and reliably determine the concentration of airborne alcohol molecules within the interior compartments of stationary and moving vehicles to thereby detect for the presence of persons in such vehicles under the influence of alcohol. In this regard, the present invention combines techniques of wavelength modulation, harmonic detection and signal processing. The resulting system is characterized by a detection sensitivity to levels of airborne alcohol molecules indicative that an occupant of a vehicle is under the influence of alcohol in excess of statutory limits. With such information, the police can reliably select which vehicles to stop for further investigation as to whether it is the driver that is under the influence of alcohol.

With the present invention, a modulated laser beam is transmitted through the interior compartment of a vehicle, received and processed to provide an indication of whether a person in the vehicle is under the influence of alcohol. The system components may be assembled in various physical configurations to meet the requirements of local operating environments. In one embodiment of the present invention, a laser beam is directed to pass through the interior compartment of a vehicle from the transmitter directly to the receiver. Alternatively, the beam can be redirected by a retro-reflective device after passing from the transmitter through the vehicle compartment, to permit the beam to be returned to the receiver located near the transmitter. This flexibility of positioning permits the present invention to be adapted to use in densely populated areas using the sobriety check point technique for example, or to be deployed adjacent to a highway and by using a retro-reflector, detect the alcohol level in the operator compartment of a passing vehicle. The sensitivity of the present invention permits reliable, repeatable quantitative detection, thereby establishing probable cause for vehicle detention and a confirming inspection.

The invention, therefore, overcomes the disadvantages at the current sobriety check points by providing instantaneous low level alcohol concentration detection, applicable to vehicles either stationary or moving at highway operating speeds.

More particularly, the analyzing system of the present invention comprises a transmitter of coherent wavelength modulated energy in the form of a laser beam, a receiver for receiving and extracting a modulation signal introduced on the beam by absorption of alcohol molecules as the beam travels through the operator compartment of the vehicle, a signal processing system for analyzing and indicating the detected concentration of airborne alcohol molecules to a system user, and structure for containing the system components and providing for ease of movement to and positioning at a desired site. Preferably, the laser beam is wavelength modulated by a modulator over the full width at half-maximum of an alcohol absorption line. A detector in the receiver is phase-locked to the modulator for the laser to only detect modulation harmonics of the laser beam. Such a technique permits detection of very low levels of alcohol molecule concentrations by eliminating signals that are not wavelength dependent and by removing background noise.

DESCRIPTION OF PREFERRED EMBODIMENTS

The analyzer system of the present invention is capable of detecting the presence of airborne alcohol molecules at concentrations in the order of 0.5 parts per million. This is comparable to the currently estimated minimum levels of airborne alcohol molecule concentrations in the interior compartment of a typical passenger car containing an occupant under the influence of alcohol in excess of the statutory limit.

Figure 1:
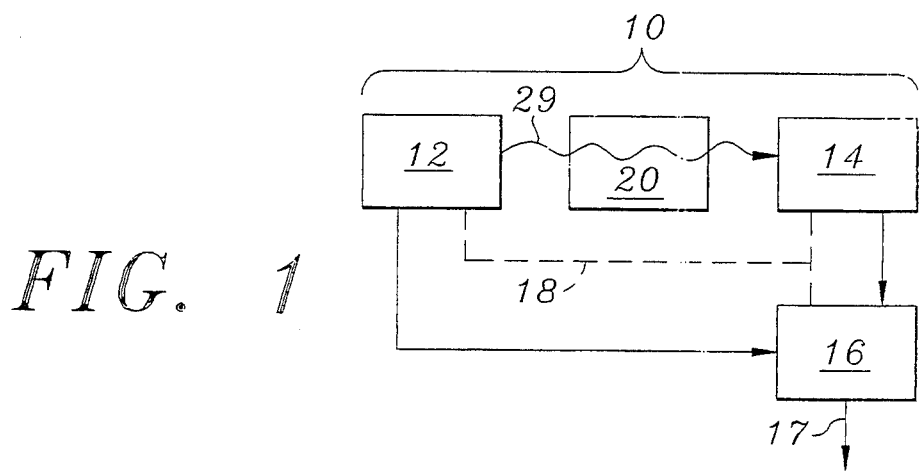
FIG. 1 is a simplified block diagram identifying the principal functional apparatus of the detection and analyzer system of the invention.

As shown in FIG. 1, the analyzer system 10 of the present invention basically comprises a coherent modulated energy source or transmitter 12, a receiver 14, a signal processing system 16 and a supporting structure 18. In operation, the transmitter 12 develops and transmits a coherent energy beam 29 through a confined volume of air 20, such as the interior compartment of a passenger vehicle, for reception by the receiver 14. The receiver 14 detects the received beam for processing by the signal processing system 16. The output 17 of the processing system 16 may be utilized to display or otherwise indicate to a system user the concentration of airborne alcohol molecules in the confined volume 20 and hence the presence of a person within the vehicle under the influence of alcohol.

Figure 3:
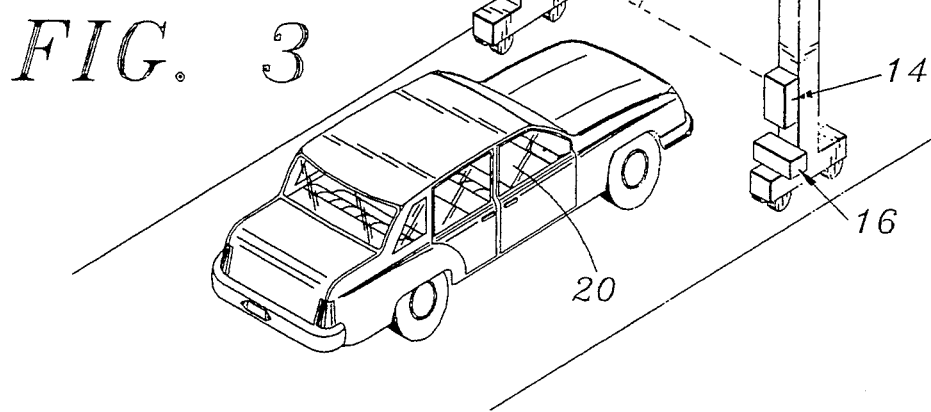
FIG. 3 is an isometric view of a first preferred embodiment of the analyzer system of the present invention for use in a populated area, showing the placement of its structural and electronic elements in relation to a typical passenger vehicle moving toward a laser beam generated by the analyzer system.
Figure 4:
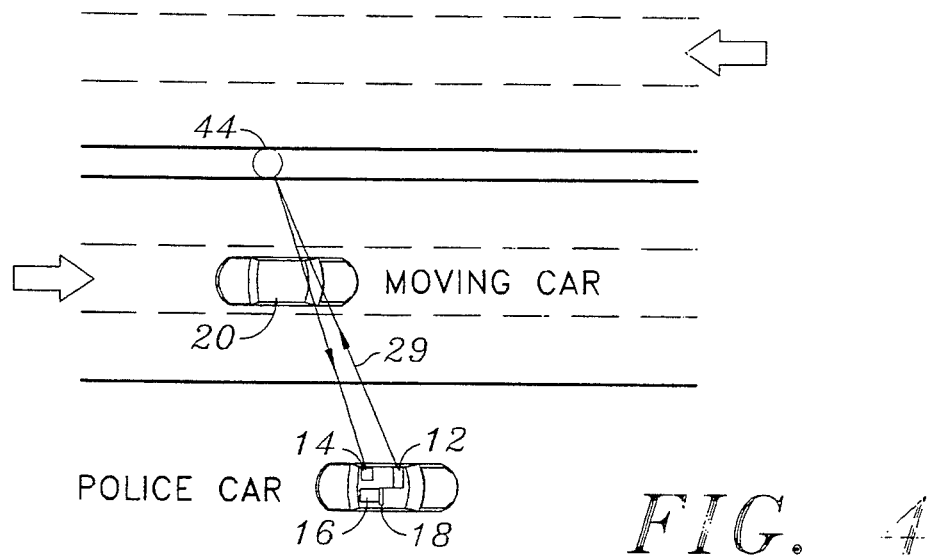
FIG. 4 is a plan view of a second preferred embodiment of the analyzer system of the present invention showing placement of its principal electronic elements in a typical highway environment.

The supporting structure 18 for the analyzer system 10 may take a variety of forms. In FIG. 3 the structure is of an inverted U-shape and provides the mechanical support and containment for positioning the transmitter 12 and the receiver 14 on opposite sides of a detection station through which a vehicle may pass and also serves to support the signal processing system 16. An alternative and significantly different mechanical support arrangement 18 may be installed in a police car as shown in FIG. 4. Such a system arrangement uses a laser beam retro-reflector 44 and permits the transmitter 12 and the receiver 14 to be conveniently mounted in adjacent locations with the signal processing system 16 within the police car to detect the concentration of alcohol molecules within the interior compartment of a moving car passing between the police car and the retro-reflector 44.

Figure 2:
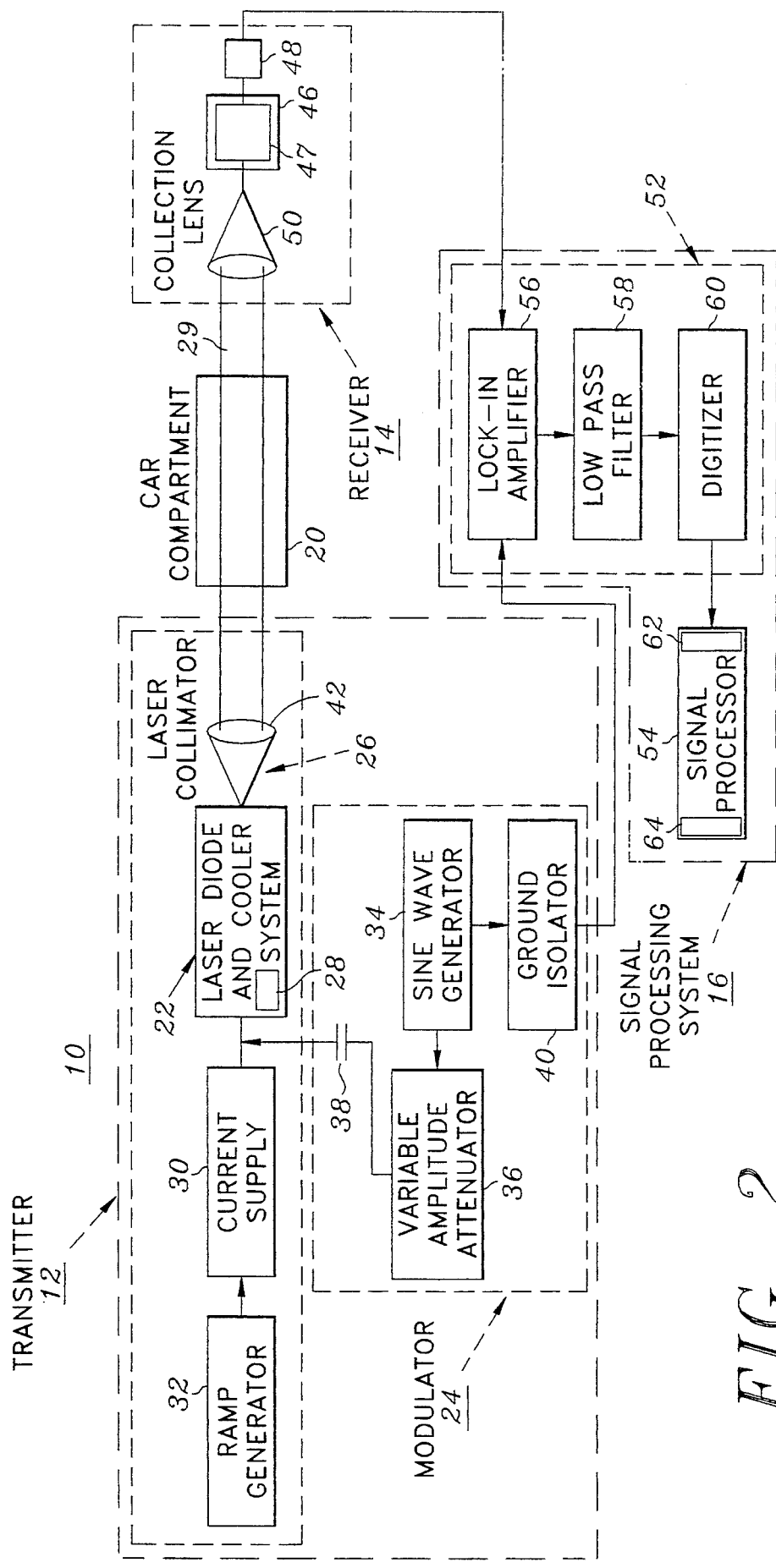
FIG. 2 is a more detailed block diagram of the analyzer system depicted in FIG. 1.

Preferably, as shown in FIG. 2, the transmitter 12 included in the analyzer system 10, comprises a laser 22, a modulator 24, and a beam collimator 26.

The laser 22 preferably comprises a single mode semiconductor diode laser. The laser may be a model MDS-2000 manufactured by Mutek of Herrsching, Germany when the analyzer system is designed to operate around the 3.39 um alcohol absorption line, or a model TSL-300 manufactured by Santec of Holmdel, N.J. when the analyzer system is designed to operate around the 1.5 um alcohol absorption line, as will be described in detail hereinafter. In either case, the laser is tunable within the infrared spectrum and housed in a liquid nitrogen cryostat cooler 28 (e.g., a Mutek MDS-1150-LN2) with a zinc selenide window through which a laser beam 29 is radiated. Additionally, the laser 22 preferably comprises a regulated current power supply 30, such as a Mutek MDS-1550, controlled by a ramp generator 32, such as a model HP8657B manufactured by Hewlett Packard Company of Santa Clara, Calif.

The modulator 24 preferably comprises a sine wave generator 34, such as a SRS DS345 manufactured by Stanford Research Systems of Sunnyvale, Calif., a variable attenuator 36, such as a Cermet trimming potentiometer model 3252 manufactured by Allied Electronics of Fort Worth, Tex., a coupling capacitor 38 (20 nF), and a signal processing isolator 40, such as a 1:1 transformer model 928-0325 manufactured by Stancor and distributed by Allied Electronics.

The beam collimator 26 preferably comprises an f/1 zinc selenide aspheric collimating lens 42, such as Mutek MDS-1125, for directing the laser beam 29 through the confined volume of air 20 in the interior compartment of a vehicle.

Optionally, as shown in FIG. 4, a retro-reflector 44 manufactured by BSA Technology Inc., Torrance Calif., may be included in the analyzer system 10 of the present invention. As shown, the retro-reflector 44 is mounted on a side of a roadway opposite the interior compartment of a moving vehicle comprising the confined volume 20, to redirect the laser beam 29 to the receiver 14 in a stationary police car which houses the transmitter, receiver and signal processing system.

The receiver 14 preferably comprises a detector 47 housed in a liquid nitrogen cooler 46, and a low noise pre-amplifier 48. When the system is designed to operate around the 3.39 um alcohol absorption line, the detector 47 may have an indium antimonide photodiode, such as a model J10D, manufactured by EG&G Judson of Montgomeryville, Pa. When the system is designed to operate around the 1.5 um alcohol absorption line, the detector 47 may have an indium arsenide photocathode such as model J12 manufactured by EG&G Judson. The cooler 46 may be a liquid nitrogen Dewar, EG&G Model M204 equipped with a sapphire window for admitting the laser beam. The low noise pre-amplifier 48, may be a model PA9 also manufactured by EG&G Judson. The receiver 14 may further comprise an f/4 zinc selenide collecting lens 50 available from BSA Technology Inc., for focusing the laser beam 29 on the detector 47. Briefly, the detector 47 receives the modulated laser beam 29 from the collecting lens 50 and passes its output to the amplifier 48 for processing in the signal processing system 16.

The signal processing system 16 preferably comprises a signal conditioner 52 and a signal processor 54. The signal conditioner 52 may comprise a lock-in amplifier 56, such as model SR530, and a low pass filter 58, such as model SR640, both manufactured by Stanford Research Systems, and a digitizer 60, such as model MAD100, manufactured by Markenrich of Duarte, Calif., for adapting the output of the signal conditioner 52 to digital processing. The signal processor 54 preferably comprises a digital computer 62 and indicating lights 64, such as model 931-4005 available from Allied Electronics, for providing and indication of the airborne alcohol molecule concentrations detected by the analyzer system 10. The computer 62 may be an IBM 486 equipped with a fast co-processor board, such as model Number Smasher 860, and NDP-Fortran 860 software manufactured by Microway of Kingston, Mass.

As previously indicated, the alcohol analyzer system 10 of the present invention uses wavelength modulation absorption spectroscopy. The operating range of the laser included in the system is selected to operate around one of the rotational vibrational transitions (absorption line) within the alcohol strong absorption bands. These bands occur in the 1.5 um, 2.74 um, 3.39 um, 7.2 um, 8.05 um and 9.5 um regions of the spectrum. Water vapor has a strong absorption band near 2.74 um, thus eliminating that wavelength as a candidate. Carbon dioxide interferes with alcohol absorption near 7.2 um. The 8.05 and 9.5 um bands present other special problems such as laser and detector cooling requirements and laser transmission deficiencies through the window of a vehicle. As a result, the absorption lines within the 1.5 um and 3.39 um bands are utilized in the present invention because lasers and detectors at these wavelengths do not have stringent cooling requirements and are readily available in the marketplace. Moreover, these wavelength bands are relatively free from interference from other gases. Also, absorption lines within these two bands may be scanned within one laser cavity mode at their respective wavelengths.

Thus, in the system of the present invention as shown in FIG. 2, the laser 22 is selected to operate around either the 1.5 um or 3.39 alcohol absorption lines. The stable current supply 30 maintains the unmodulated laser 22 operating point at the quiescent wavelength. The ramp generator 32 controls the operating cycle of the laser 22 by applying control pulses which turn the laser on and off. The modulator 24 controls the laser 22 wavelength around its quiescent point with a signal provided by the sine wave generator 34. The sine wave is applied to the current supply 30 of the laser 22 through the variable attenuator 36 and the capacitor 38. The attenuator 36 establishes the appropriate range of modulation, thereby determining the excursion of the wavelength of the beam generated by the laser 22. Capacitor 38 isolates the direct current from the current supply 30 while permitting the application of the modulating voltage to the laser 22. The sine wave is simultaneously applied to the lock-in amplifier 56 for phase-lock detection of the laser beam modulation.

The beam 29 from the laser 22 is applied to the collimator 26. The aspheric lens of the collimator 26 directs the laser beam 29 through the vehicle passenger compartment 20 and the contained alcohol molecules.

The preferred embodiment as shown in FIGS. 2 and 3, depicts the receiver 14 in a straight line location on the opposite side of the vehicle compartment 20 to intercept the beam 29. As the laser beam 29 exits the vehicle compartment 20, the beam is intercepted by the collecting lens 50, and thereby focused on the detector 47. The output from the detector 47 comprises the modulation products imposed on the laser beam 29 as it passes through the vehicle compartment 20. Preamplifier 48 provides low noise amplification to the detected modulation products, thereafter applied to the lock-in amplifier 56. The lock-in amplifier 56, phase-locked to the sine wave generator 34 further demodulates the modulation products from the detector 47. The residual signal is applied to the low pass filter 58 to remove undesired high frequency demodulation products. From the low pass filter 58, the signal is digitized in the digitizer 60 for storage and processing in the computer 62, part of the signal processor 54. The analytical result is provided to a user of the system 10 by the indicator lights 64.

In the embodiment of FIG. 3, the support structure 18 for the system straddles a lane of traffic as in a sobriety checkpoint more appropriately adapted to streets in a metropolitan area. The structure 18 also provides for vertically positioning the transmitter 12 and receiver 14 to permit the laser beam 29 to pass through the vehicle compartment 20. The structure 18 is also moveable to permit its easy transport from site to site and positioning at a particular site.

In the embodiment depicted in FIG. 4, the transmitter 12, receiver 14 and signal processing system 16 are supported by the structure 18 within a police car positioned adjacent to a highway. The retro-reflector 44 is placed across the lanes of one-way traffic at a suitable height to intercept the laser beam 29 directed at a slight rearward angle from the transmitter 12 across the highway. The retro-reflector 44 receives and returns the laser beam 29 to the receiver 14 and thence to the signal processing system 16 for indication of the analytical result of the signal processing to those in the police car.

Accordingly, the present invention provides an improved, highly reliable method and system for non-invasively determining the concentration of airborne alcohol molecules in the interior compartments of vehicles and for determining in real-time the presence of a person within a vehicle under the influence of alcohol.

We claim:

1. A non-intrusive method of detecting the sobriety of a person in a vehicle, comprising:
    generating and transmitting a beam of electromagnetic energy through an interior compartment of a vehicle containing airborne alcohol molecules emitted by a person in the vehicle;
    detecting the beam after it has passed through the compartment;
    processing the detected beam to determine the concentration of the airborne alcohol molecules in the compartment and hence the sobriety of a person in the vehicle.

2. The method of claim 1 wherein:
    the generating of the beam includes generating a wavelength modulated laser beam, and
    the detecting of the beam is with a detector phase-locked with the modulation frequency of the laser beam.

3. The method of claim 2 wherein the generating of the beam includes modulating the beam over the full width at half maximum of an absorption line for alcohol.

4. The method of claim 3 wherein the alcohol absorption line is within the 1.5 um band or the 3.39 um band.

5. The method of claim 1 further including reflecting the beam after it passes through the compartment to apparatus for detecting the beam.

6. A non-intrusive system for detecting the presence of a person in a vehicle under the influence of alcohol, comprising:
    transmitter means for generating and transmitting a coherent wavelength modulated energy beam through an interior compartment of a vehicle;
    receiver means for (i) intercepting the beam after it has passed through the compartment, (ii) extracting modulation introduced by airborne alcohol molecules in the compartment, and (iii) developing an output signal representative of such modulation; and
    signal processing means for analyzing the output signal from the receiver means and for indicating to a user of the system the concentration of airborne alcohol molecules in the compartment and hence the sobriety of a person in the vehicle.

7. The system of claim 6 further including structure means for positioning the transmitter means on one side of the compartment and the receiver means on the other.

8. The system of claim 6 further including retro-reflector means for reflecting the beam after it passes through the compartment to the receiver means and structure means for positioning the retro-reflector means and the receiver means on opposite sides of the compartment.

9. The system of claim 6 wherein the transmitter means comprises:
   laser means for emitting a coherent electromagnetic beam;
   modulator means for varying the wavelength of the emitted laser beam in a predetermined manner and for producing a modulator signal; and
   focusing means for collimating and aiming the laser beam through the compartment to the receiver means.

10. The system of claim 9 wherein the receiver means comprises:
    a photo-detector means with spectral sensitivity for detecting the coherent electromagnetic beam emitted by the laser and for generating a detector signal; and
    collecting means for capturing the laser beam for application to the photo-detector means.

11. The system of claim 10 wherein the signal processing means comprises:
    signal conditioning means for correlating signals generated by the photo-detector means and the modulator means for subsequent processing; and
    computer means for correlation processing the detector and modulator signals and for determining laser energy absorption in the interior compartment of the vehicle.

12. The system of claim 11 wherein the signal conditioning means comprises:
    a demodulation amplifier for combining the detector signal with a sine wave signal for correlation of the transmitted laser beam and the detected laser beam;
    a filter for removing undesired demodulation products; and
    a digitizer for producing digital signals suitable for subsequent processing.

13. The system of claim 12 wherein the computer means comprises:
    a digital computer for analyzing and correlating the digital signals and generating user information; and
    indicator lights for presenting information suitable for use by a user of the system.

14. The system of claim 10 wherein the photo-detector means comprises:
    a detector for detecting any residual laser beam energy and producing an output signal of modulation products after the laser beam transverses the interior compartment of the vehicle;
    a cooled container for maintaining the detector at a proper operating temperature with a window for admitting the laser beam; and
    a pre-amplifier for converting an output current from the detector for subsequent processing by the signal processing means.

15. The system of claim 14 wherein the collecting means comprises a lens for focusing the received laser beam into the detector.

16. The system of claim 9 wherein the laser means comprises:
    a semiconductor laser diode operating at a wavelength for generating a coherent electromagnetic energy beam compatible with an ethyl alcohol absorption line;
    a regulated power supply and a ramp generator for controlling the laser wavelength and amplitude of operation; and
    a cooler for containing the laser diode at optimal operating temperature with a window for providing an exit port for the laser beam.

17. The system of claim 9 wherein the modulator means comprises:
    a sine wave generator for providing a sinusoidal voltage for modulating an operating power supply for the laser means and thereby varying the laser operating wavelength;
    a variable attenuator for controlling the amplitude of the sinusoidal voltage applied to the laser power supply;
    a modulation coupler for inserting the sinusoidal voltage into the laser power supply; and
    a signal processing isolator for isolating and applying the sinusoidal voltage to the signal processing means.

18. The system of claim 9 wherein the focusing means comprises:
    a collimating lens for directing the laser beam through the interior of the vehicle; and
    a retro-reflector for redirecting the laser beam passing through the interior compartment to the receiver means.

* * * * *